United States Patent
Rao et al.

(10) Patent No.: US 10,948,414 B2
(45) Date of Patent: Mar. 16, 2021

(54) METHOD AND APPARATUS FOR RAPID DETECTION OF BACTERIAL CONTAMINATION

(71) Applicant: UNIVERSITY OF MARYLAND, BALTIMORE COUNTY, Baltimore, MD (US)

(72) Inventors: Govind Rao, Ellicott City, MD (US); Yordan Kostov, Ellicott City, MD (US); Mustafa Al-Adhami, Silver Spring, MD (US); Chandrasekhar Gurramkonda, Baltimore, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 231 days.

(21) Appl. No.: 16/000,935

(22) Filed: Jun. 6, 2018

(65) Prior Publication Data
US 2018/0348131 A1  Dec. 6, 2018

Related U.S. Application Data

(60) Provisional application No. 62/515,598, filed on Jun. 6, 2017.

(51) Int. Cl.
*G01N 21/64* (2006.01)
*B01L 3/00* (2006.01)
*G01N 21/01* (2006.01)
*G01N 21/27* (2006.01)

(52) U.S. Cl.
CPC ...... *G01N 21/6428* (2013.01); *B01L 3/50273* (2013.01); *B01L 3/502715* (2013.01); *B01L 3/502753* (2013.01); *B01L 3/502761* (2013.01); *G01N 21/645* (2013.01); *B01L 2300/044* (2013.01); *B01L 2300/0681* (2013.01); *B01L 2300/0816* (2013.01); *B01L 2300/0867* (2013.01); *B01L 2400/0487* (2013.01); *C12Q 2304/22* (2013.01); *G01N 21/272* (2013.01); *G01N 21/6408* (2013.01); *G01N 2021/0112* (2013.01); *G01N 2201/0221* (2013.01); *G01N 2333/195* (2013.01)

(58) Field of Classification Search
CPC .... G01N 21/6428; G01N 21/64; G01N 21/63; G01N 21/61; B01L 3/502715; B01L 3/5027; B01L 3/502; B01L 3/50
USPC ...................................... 422/503, 50; 436/43
See application file for complete search history.

(56) References Cited

U.S. PATENT DOCUMENTS

| | | | |
|---|---|---|---|
| 8,980,199 B2 * | 3/2015 | Imran | B01J 19/0093 422/505 |
| 2013/0183209 A1 * | 7/2013 | Richter | A61M 5/16877 422/403 |

OTHER PUBLICATIONS

Gurramkonda et al, Fluorescence-based method and a device for rapid detection of microbial contamination , PDA J Pharm Sci Technolo, 2014, 68(2), pp. 164-171. (Year: 2014).*

(Continued)

*Primary Examiner* — Christine T Mui
(74) *Attorney, Agent, or Firm* — Tristan A. Fuierer; Olive Law Group, PLLC

(57) ABSTRACT

A device and method for detecting the presence of bacteria in a sample are provided. A multi-step process for sample preparation is utilized and a microfluidic device is disclosed. The detection is performed using microfluidics and physical changes in multiple samples in differential mode.

14 Claims, 5 Drawing Sheets

(56) References Cited

OTHER PUBLICATIONS

Pharmtech.com (2015) An overview of rapid microbial-detection methods|Pharmaceutical technology. N.p. 2015. Web. Jun. 3, 2015.
Hoehl MM et al (2012) Rapid and robust detection methods for poison and microbial contamination. J Agric Food Chem 60 (25):6349-6358.
Hobson Ns, Tothill I, Turner Ap (1996) Microbial detection. Biosens Bioelectron 11 (5):455-477.
Fda.gov (2015) Archived BAM method: rapid methods for detecting foodborne pathogens. N.p. Web. Jul. 23, 2015.
Vogel Sj, Tank M, Goodyear N (2013) Variation in detection limits between bacterial growth phases and precision of an ATP bioluminescence system. Lett Appl Microbiol 58 (4):370-375 Web.
Celsis.com (2010) Quality control—microbial testing: rapid microbiological methods in lean manufacturing. N.p. Web. Jul. 23, 2015. Can Not Locate.
Pettit Ac, Kropski Ja, Castilho Jl, Schmitz Je, Rauch Ca, Mobley Bc, Wang Xj, Spires Ss, Pugh Me (2012) The index case for the fungal meningitis outbreak in the United States. N Engl J Med 367(22):2119-2125.
Gurramkonda C et al (2014) Fluorescence-based method and a device for rapid detection of microbial contamination. PDA J Pharm Sci Technol 68(2):164-171 Web. Abstract.
Estes C, Duncan A, Wade B, Lloyd C, Ellis W Jr, Powers L (2003) Reagentless detection of microorganisms by intrinsic fluorescence. Bio-sens Bioelectron 18(5):511-519.
Bionity.com (2015) Alamarblue® assay for assessment of cell proliferation using the Fluos-tar Optima. N.p. Web. Jul. 23, 2015.
Boyce St, Anderson Ba, Rodriguez-Rilo Hl (2006) Quantitative assay for quality assurance of human cells for clinical transplantation. Cell Transplant 15(2):169-174.
Nagaoka M, Hagiwara Y, Takemura K, Mura-kami Y, Li J, Duncan Sa, Akaike T (2008) Design of the artificial acellular feeder layer for the efficient propagation of mouse embryonic stem cells. J Biol Chem 283 (39):26468-26476.
Longhi Mp, Wright K, Lauder Sn, Nowell Ma, Jones Gw, Godkin Aj, Jones Sa, Galli-more Am (2008) Interleukin-6 is crucial for recall of influenza-specific memory CD4 T cells. PLoS Pathog 4(2):e1000006.
Tanaka Tq, Williamson Kc (2011) A malaria gametocytocidal assay using oxidoreduction indicator, alamarBlue. Mol Biochem Parasitol 177(2)160-163.
Hudman Da, Sargentini Nj (2013) Resazurin-based assay for screening bacteria for radiation sensitivity. Springerplus 2(1):55.
Fields Rd, Lancaster Mv (1993) Dual-attribute continuous monitoring of cell proliferation/cytotoxicity. Am Biotechnol Lab 11 (4):48-50. Can Not Locate.
Al-Adhami, M et al., Rapid Detection of Microbial Contamination Using a Microfluidic Device, Biosensors and Biodetection: Methods and Protocols vol. 1: Optical-Based Detectors, Methods in Molecular Biology, vol. 1571, DOI 10.1007/978-1-4939-6848-0_18, 2017, Chapter 18.

* cited by examiner

Resazurin

Viable Cells
(Reduction Reaction)

Resorufin

METHOD AND APPARATUS FOR RAPID DETECTION OF BACTERIAL CONTAMINATION

CROSS REFERENCE TO RELATED APPLICATIONS

This application is filed under the provisions of 35 U.S.C. § 111(a) and claims priority to U.S. Provisional Patent Application No. 62/515,598 filed on Jun. 6, 2017 in the name of Mustafa Al-Adhami and entitled "Method and Apparatus for Rapid Detection of Bacterial Contamination," which is hereby incorporated by reference herein in its entirety.

STATEMENT REGARDING FEDERALLY SPONSORED RESEARCH

Portions of this invention may have been financially supported by the United States Government support under a grant from the U.S. Food & Drug Administration under Grant Number UO1-MD-0022012.

FIELD

The present invention relates to a method of detecting the presence of viable cells in a sample, and a device that is useful for said detection. Advantageously, the device is microfluidic and as such, the system for detecting the presence of viable cells can be compact, portable, and/or hand-held and permits the user to identify if viable cells (e.g., microorganisms) are present in the sample within minutes.

BACKGROUND OF THE INVENTION

Each year, thousands of people die and millions are sickened due to food, water, or medicine contamination [1]. In order to prevent most of these poisonings, a rapid, precise and sensitive microbial detection method is highly desirable [2,3]. There are many common methods to detect pathogens and other biologics [4]. Most of these methods require well-equipped and environmentally stable laboratories as well as highly trained staff to handle devices and reagents or antibodies [4]. These methods are hard to apply in the field, especially for products that have to be sterile to prevent infection of the patients [1,5]. For many industries, the late detection of contamination can be costly. Therefore, it is vitally important to develop a method and apparatus that can detect contamination rapidly and is robust enough to utilize in the field. Detecting the contamination at an early stage can save both time and labor for the manufacturer and more importantly, increases the safety of the final product. For example, having near-real-time feedback of possible contamination in bioreactors can be very critical since each batch takes many days to grow before harvest and it would be of great interest to abort the process early in case of contamination [6]. The device could be used for multiple applications, some of which are described below.

A proposed application of rapid microbial detection is in the quality control processes for biopharmaceuticals. Since biologics are highly susceptible to contamination by adventitious agents such as viruses or mycoplasma, there is a need for risk mitigation procedures such as testing to confirm the absence of any unwanted contaminants [7]. This way, contaminated products can be caught early, which minimizes the risk of having them produced and then sold in pharmacies. Furthermore, rapid microbial detection could be used during the biological process to test manufactured drugs for contamination [8].

Cholera is an acute infection caused by the ingestion of food or water contaminated with the bacterium *Vibrio Cholerae*. It has been estimated that each year there are 1.3-4.0 million cases of cholera, with approximately 100,000 deaths. The incubation period of the cholera bacteria is 12 hours to 5 days. In severe cases, cholera can kill a person within an hour of showing symptoms. It can be hard to diagnose a patient with cholera since the symptoms are similar to other diseases, for example acute watery diarrhea. However, it is very important to detect cholera early because of the potential for a widespread outbreak. The best way to prevent cholera is to detect it in water before it enters the body. Traditionally, to test for water sterility, all water specimens have been collected in temperature-controlled containers and transported to a laboratory. Large volumes of water are needed for better pathogen detection. The most common way to detect the contamination is by direct cell culture, wherein the contaminated sample is diluted with alkaline peptone water (APW), incubated at 35° to 37° C., and then plated for 6-8 hours. Alternatively, 100-300 mL of water sample is filtered through 0.22-0.45 μm membrane (Millipore) filters and then the filter placed in 100 mL of APW in a flask. The sample is then incubated for 6-8 hours and then plated for 18 to 24 hours at 35° to 37° C. Accordingly, most assays to detect cholera in water samples are time consuming, expensive, and require highly trained lab technicians, and are not sensitive enough to detect low concentrations of bacterial contaminants. Moreover, the current methods of detecting cholera are not useful in the field where rapid and reliable cholera detection is most needed. A portable device that can timely and sensitively detect the presence or absence of *Vibrio Cholerae* in water samples is therefore needed to prevent cholera from spreading, especially in regions with limited or no laboratories.

In some infections, for example sepsis, evidence of contamination can be delayed, resulting in an increased risk of developing septic shock, which is associated with high mortality rates. Sepsis usually affects the young, the old, and those with a weak immune system. When a patient is determined to have sepsis, there is a response bundle that medical professionals follow to fight against the infection. The key to fighting sepsis is to start antibiotics early. Broad spectrum antibiotics are usually prescribed to these patients to cover all likely pathogens while blood samples are being tested. Preferably, a method of contamination detection will allow for the rapid determination of the sepsis infection so that the best antibiotic can be prescribed immediately.

Presently, "rapid" methods of contamination detection take approximately 24 hours. For example, in the case of the polymerase chain reaction (PCR), it has been stated in the protocol that it can be used to detect the viable cells present only in the exponential phase. PCR is very labor intensive and takes approximately 27 hours to achieve results. Although PCR can detect contamination of colony forming units as low as 10 CFU, it is not clear whether the detected cells are dead or alive at the time of detection. There are other reported methods that are faster, for example measuring the intrinsic fluorescence of the bacterial or yeast chromophores [9]. This approach is fast and sensitive but it is limited to a slightly higher number of colony forming units and it is very specific, requiring a high level of knowledge about the environment in which the contamination is detected to compensate for background signal.

Additionally, other properties that can be monitored to determine the metabolic rate of viable cells include pressure, pH, carbon dioxide detection, fluorescence, and absorbance. Negative pressure detection in enclosed containers has been used to detect bacteria, in which electronic transducers are used. Another way is by using pH sensitive hydrogels inside cuvettes where the bacterial growth is correlated to the pH changes in the system. Detecting the level of $CO_2$ in the medium is also a way to determine the metabolic rate. Indicator dyes could also be used to detect the metabolic rate of bacteria. Indicator dyes are also used to detect viable cells in samples where fluorescence or absorbance is monitored.

There remains the need in the art of contamination detection for a device and a method of using same that is able to detect the presence of viable cells in samples rapidly. This device may be compact, portable, and/or hand-held, and may detect changes in fluorescence, absorbance, temperature, pressure, pH, conductivity and/or image processing using a mobile phone, tablet, or computer.

SUMMARY OF THE INVENTION

In a first aspect, a microfluidic cassette is described, said cassette comprising: at least two channels, wherein a first channel is communicatively connected to a first chamber and a second channel is communicatively connected to a second chamber, wherein the cassette further comprises at least one inlet injection port and each channel has a dedicated outlet injection port, wherein each injection port has a septum.

In another aspect, a kinetic fluorometer system is described, said system comprising:
an excitation module comprising a light source and a voltage-controlled current source;
a microfluidic cassette;
an excitation filter mounted between the light source and the microfluidic cassette;
a detector positioned 90° relative to the excitation light path from the light source;
an emission filter positioned between the detector and the microfluidic cassette; and
a microprocessor.

In still another aspect, a method of detecting the presence of viable cells in a sample is described, said method comprising detecting a physical property of a sample and a sample-derived negative control and comparing same to determine a differential rate, wherein the differential rate is indicative of the presence of viable cells in the sample.

Other aspects, features and embodiments of the invention will be more fully apparent from the ensuing disclosure and appended claims.

DETAILED DESCRIPTION, AND PREFERRED EMBODIMENTS THEREOF

Figure 1A:
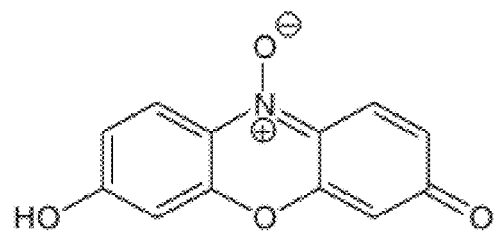
FIG. 1A illustrates the reduction of resazurin to resorufin.
Figure 1A:
Figure 1A:
Figure 1A:
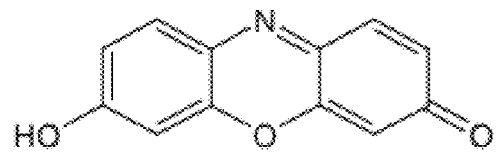
Figure 1B:
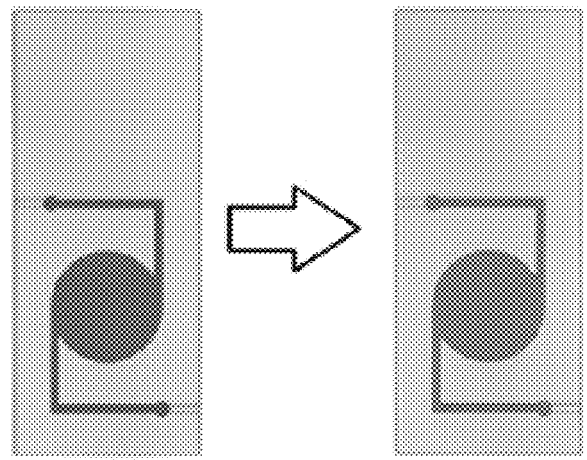
FIG. 1B illustrates the color transformation when resazurin is converted to resorufin.

The present invention relates to a device and method that can detect microorganism contamination in samples by detecting the metabolic activity of viable cells. Advantageously, the device and method allows the user to compare the sample to a sample-derived negative control concurrently and simultaneously. This device may be compact, portable, and/or hand-held, and may detect changes in fluorescence, absorbance, temperature, pressure, pH, conductivity and/or image processing using a mobile phone, tablet, or computer.

As defined herein, a "sample-derived negative control" corresponds to the sample wherein any viable cells have been inactivated or removed. For example, the cells can be removed using a microfilter or centrifugation or other microfluidic-based cell separation methods, as readily understood by the person skilled in the art. Mammalian cells can be simply sedimented, e.g., left in a container for a period of time with a blood thinner, e.g., heparin, added to the blood to minimize clotting. As defined herein, the sample-derived negative control is preferably substantially devoid of viable cells.

As defined herein, a "sample" corresponds to any material that is aqueous-based. The sample comprises water and may contain other substances that are soluble or dispersed in water, e.g., cells, micelles, colloidal material, etc. For example, the sample can be filtered or non-filtered water, treated or non-treated water, urine, blood, plasma, tears, aqueous-based beverages, sewage, animal lagoon water, pharmaceutical reaction solutions, milk, and any solutions comprising solubilized pharmaceuticals, contrast agents (X-ray, PET or MRI), radio nuclides, nutriceuticals, or food.

As defined herein, "cells" can include prokaryotic cells (e.g., pathogenic bacteria) and eukaryotic cells (e.g., pathogenic tumor cells).

Microorganisms that can be detected using the device and method described herein include, but are not limited to, *Escherichia coli, Listeria monocytogenes, Salmonella species* (e.g., *S. typhi*), *Vibrio cholera, Shigella* (e.g. *S. dysenteriae*), *Cryptosporidium parvum, Toxoplasma gondii, Giardia lamblia, Cyclospora cayetanensis; Pseudomonas* (e.g., *P. aeruginosa, P. putida*), *Bacillus, Clostridium* (e.g., *C. botulinum, C. tetani, C. difficile, C. perfringens*), *Corynebacterium* (e.g., *C. diphtheria*), *Arthrobacter, Lactobacillus, Microbacterium, Micrococcus, Streptococcus* (e.g., *S. pyogenes, S. pneumoniae*), *Listeria, Escherichia, Yersinia* (e.g., *Y. pestis*), *Campylobacter, Mycobacterium* (e.g., *M. tuberculosis, M. leprae*), *Staphylococcus* (e.g., *S. aureus*), *Haemophilus* (e.g., *H. influenza*), *Neisseria* (e.g., *N. meningitidis, N. gonorrhoeae*), *Chlamydia* (e.g., *C. trachomatis*), *Bordetella* (e.g., *B. pertussis*), *Treponema* (e.g., *T. palladiu*), and combinations thereof.

Depending on the sample studied, there are multiple ways in which viable cells are detected. Traditionally, a cell culture is required for most human-related samples wherein cells are grown under controlled conditions. Most of these methods are done in laboratories and require careful handling. Most cell cultures go through two important steps; cell isolation wherein the cells are extracted from the sample and cell maintenance in a culture. It is also important to monitor conditions inside the culture in case there is a change in pH levels and/or nutrient depletion. For non-human-related samples, there are devices that can detect contamination. Most of these devices can take upwards of 24 hours to analyze the samples.

What is needed is a rapid, robust, cost effective, and non-invasive device to detect metabolic changes of viable cells in samples with high sensitivity to detect low levels of contaminations and/or early stages of infections. An aspect of the device is to have a sample-derived negative control so that both the positive and negative control samples are measured simultaneously such that any difference between the two samples determines the presence of viable cells. The sample-derived negative control is created from the sample by splitting it in two portions and removing the bacteria (e.g. by filtering, centrifuging, etc.) from one of the portions. Both the sample and the sample-derived negative control are loaded at the same time in separate microfluidic chambers, mixed with the same amount of indicator dye, and kept at the same conditions (e.g., temperature, pressure, etc.). The difference in the conversion rates of Resazurin, termed differential rate, is monitored. By using the differential rate, it is possible to test any type of sample regardless of the medium, while removing the effects of possible interfering substances. Advantageously, the device and method does not rely on the use of traditional plate-based assay tests to verify the results.

Broadly, a microfluidic device and method of using same is described, wherein the microfluidic device has two channels, one for unaltered sample and one for the sample-derived negative control, wherein each channel is communicatively connected to at least one dedicated chamber. The method uses the difference in at least one physical property between the sample and the sample-derived negative control to detect the presence of viable cells (i.e., the metabolic activity of the sample) in the sample. The device may detect changes in fluorescence, absorbance, temperature, pressure, pH, conductivity and/or image processing in the sample and then compare it to the sample-derived negative control. The device provides for the reliable detection of contamination in less than about 30 minutes.

The device does not identify the species or the growth phase of the cells that are detected. The main purpose of the device is to detect viable cells in the tested samples. Having the ability to rapidly screen a variety of samples irrespective of the contaminating species is of great value to many industries and municipalities. The device and method have proven to be accurate and fast, which makes it suitable for rapid detection of contamination applications.

It should be appreciated by the person skilled in the art that the time of the measurement of the at least one physical property can be variable, from time in a range from about 1 minute to about 240 minutes, preferably from about 1 minute to about 30 minutes for a vigorously growing aerobe and about 60 minutes to about 240 minutes for barely viable, low respiration rate cells.

In one aspect, a microfluidic cassette is described, said microfluidic cassette comprising: at least two channels, wherein a first channel is communicatively connected to a first chamber and a second channel is communicatively connected to a second chamber, wherein the cassette further comprises at least one inlet injection port and each channel has a dedicated outlet injection port, wherein each injection port has a septum.

As will be described below in the examples, the microfluidic cassette can comprise a fork defining the first channel and the second channel subsequent to the inlet injection port, or can comprise a first inlet injection port for the first channel and a second inlet injection port for the second channel.

In a second aspect, a kinetic fluorometer system is described, said system comprising:
an excitation module comprising a light source and a voltage-controlled current source;
a microfluidic cassette;
an excitation filter mounted between the light source and the microfluidic cassette;
a detector positioned 90° relative to the excitation light path from the light source;
an emission filter positioned between the detector and the microfluidic cassette; and
a microprocessor.

The microfluidic cassette described herein can be used in the kinetic fluorometer system or alternatively, a different microfluidic cassette can be used in said fluorometer system.

In a third aspect, a method of detecting the presence of viable cells in a sample is described, said method comprising detecting a physical property of a sample and a sample-derived negative control and comparing same to determine a differential rate, wherein the differential rate is indicative of the presence of viable cells in the sample. The method further comprises loading the sample and the sample-derived negative control in a microfluidic cassette, wherein the microfluidic cassette described herein can be used in the method of detecting or alternatively, a different microfluidic cassette can be used in said method, so long as there are two separate chambers for detecting physical properties of the sample and the sample-derived negative control in the microfluidic cassette. Advantageously, if the sample has been prepared to include an increase in a concentration of viable cells therein, there is an increased sensitivity of the detecting of the presence of viable cells in the sample.

Recently, resazurin has been found to be an inexpensive compound that can provide a fluorescent readout at good sensitivity [10, 11]. Resazurin is a blue dye which itself is weakly fluorescent [10]. However, viable cells retain the ability to reduce resazurin into resorufin, which is highly fluorescent [11]. Nonviable cells do not have the metabolic capacity to reduce this indicator dye. Resazurin-based assays are used for viability detection of cells other than bacterial cells, e.g., human cells for clinical transplantation [12], stem cells [13], CD4 T cells [14], and malarial gametocytocidal assay [15]. Also, resazurin-based assays can be used for the screening of bacteria for radiation sensitivity [16].

As shown in FIG. 1, the conversion of resazurin to resorufin changes the color of the dye from blue to red, which is accompanied by a significant increase of the absorption green-yellow-green region of visible light ($\lambda_{max}$=570 nm). The fluorescence emission in the orange-red region ($\lambda_{max}$=590 nm) is enhanced as well. The conversion process provides a linear curve over a wide range of cell concentrations [17]. Accordingly, in one embodiment, the viable cells are detected in the sample using resazurin and fluorescence detection.

Advantageously, the method of use includes, but is not limited to, (i) may provide health-care facilities with a means to determine the right antibiotic to prescribe for patients suffering from different infections, e.g., sepsis, (ii) may be used to detect contamination in water samples, e.g., the presence of cholera, (iii) may be used to detect probiotics in food such as yogurt, (iv) may be used to detect food spoilers, e.g., Lamellae bacteria, and (v) may be used to detect contamination in pharmaceutical products. The device may or may not need a power source depending on the operating mode. It may be automatic or be run manually. The device may or may not be a single-use kit depending on the materials used.

Accordingly, in another aspect, a method of testing the efficacy of antibiotics is described, said method comprising detecting a physical property of (i) a sample in the presence of an antibiotic and (ii) a sample-derived negative control and comparing same to determine a differential rate, wherein a differential rate is indicative of the reduced or negligible efficacy of the antibiotic on the sample. In other words, if the antibiotic was able to kill the cells, the slope of the sample in the presence of antibiotic should be substantially zero, similar to that of the negative control. The method comprises loading the sample and the sample-derived negative control in a microfluidic cassette, wherein the microfluidic cassette described herein can be used in the method of detecting or alternatively, a different microfluidic cassette can be used in said method, so long as there are two separate chambers for detecting physical properties of the sample and the sample-derived negative control in the microfluidic cassette.

In yet another aspect, the system can be used in a method of distinguishing between antibiotic resistant and non-resistant bacterial strains, wherein if the putative bacteria are resistant, they will show viability even in the presence of the tested antibiotic, while the control bacteria will die. In this method, a physical property of (i) a viable sample in the presence of an antibiotic and (ii) an antibiotic resistant sample in the presence of the antibiotic are measured and compared to determine a differential rate, wherein a differential rate is indicative of the an antibiotic resistant sample. In this case, the differential rate is a negative slope, wherein the viable sample has a lower slope compared to the antibiotic resistant control. The method comprises loading the viable sample and the antibiotic resistant sample in a microfluidic cassette, wherein the microfluidic cassette described herein can be used in the method of detecting or alternatively, a different microfluidic cassette can be used in said method, so long as there are two separate chambers for detecting physical properties of the sample and the sample-derived negative control in the microfluidic cassette.

In another aspect, a method of determining the dose response of a strain of bacteria to an antibiotic is described, wherein the dose that kills a prescribed percentage of the bacteria is readily determined using the microfluidic cassette described herein. Being able to prescribe the correct antibiotic in the correct dose is important, as it allows to decrease the chance of developing antibiotic resistance. Prescribing the minimum needed dose to achieve the maximum effect plays an important role in the antibiotic stewardship.

In still another aspect, a method of detecting contamination in water, food, or pharmaceutical products, by-products, or intermediates is described, said method comprising detecting a physical property of a sample and a sample-derived negative control and comparing same to determine a differential rate, wherein the differential rate is indicative of the presence of viable cells or contamination in the sample. The sample comprises the water, food or pharmaceutical products, by-products, or intermediates to be tested.

In yet another aspect, a method of detecting probiotics in water or food is described, said method comprising detecting a physical property of a sample and a sample-derived negative control and comparing same to determine a differential rate, wherein the differential rate is indicative of the presence of viable cells in the sample.

The features and advantages of the invention are more fully illustrated by the following non-limiting examples, wherein all parts and percentages are by weight, unless otherwise expressly stated.

Example 1

Proof of Concept

The device prototype used as a proof of concept is a portable device that consists of two single-excitation, single-emission photometers, one for the sample and another for the sample-derived negative control. The photometers continuously measure fluorescence intensity of an indicator dye and provides a plot of same. The slope of the plot depends on the number of colony forming units per milliliter of sample. The method and device utilize resazurin as the indicator dye wherein any viable cells present in the sample reduce resazurin to resorufin, which is more fluorescent. Photodiodes were used to detect fluorescence change. The photodiode generated current proportional to the intensity of the light that reached it, and an op-amp was used in a transimpedance differential configuration to ensure amplification of the photodiode's signal. A microfluidic chip was designed specifically for the device. It acts as a fully enclosed cuvette/cassette, which enhances the resazurin reduction rate. In tests, the *E. coli*-containing media were injected into the microfluidic chip and the device was able to detect the presence of *E. coli* in LB media based on the fluorescence change that occurred in the indicator dye. The various components of the device and process are introduced below.

Portable Kinetic Fluorometer

Figure 2:
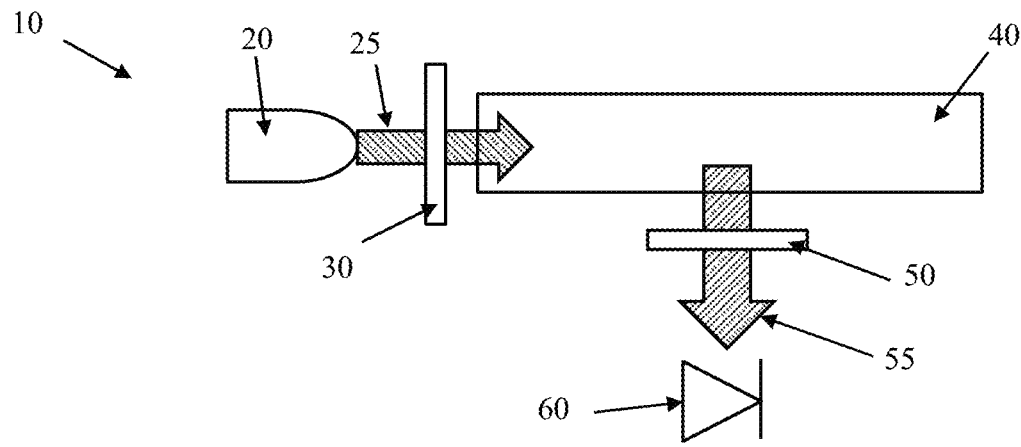
FIG. 2 illustrates the excitation and emission paths relative to the microfluidic cassette in the kinetic fluorometer.

The kinetics fluorometer is a single-excitation, single emission photometer that can detect fluorescence change in two samples and then plots the readings. A generalized schematic of the excitation module 10 of the device is shown in FIG. 2. The excitation 25 and emission 55 light paths are oriented at 90° at each other. The excitation module 10 consists of a light source, e.g., an LED, laser-diode, electroluminescent lamp, incandescent lamp, halogen lamp, sunlight, or other light source, with emission maximum of 525 nm and voltage controlled current source (not shown) which sets a constant current through the light source. An excitation filter 30 is mounted in front of the light source 20 in order to filter all the light that enters the microfluidic cassette 40. Ideally, the filter 30 and the light source 20 should be mounted in a holder that keeps them mechanically aligned. The holder is preferably made of non-fluorescent materials, A photodiode 60 is employed to detect the fluorescence intensity by generating current proportional to the intensity of the light reaching them. The photodiode should be mounted at an angle of 90 degrees to the excitation beam, with the emission filter 50 mounted in front of it. It should be appreciated that the detector should be chosen based on the physical property measured and in the present description is specific to fluorescence. The sample is loaded into the device via the microfluidic cassette 40.

Strong ambient light may interfere with device operation, even though it can be shielded (e.g., the cassette holder can be made of black plastic). Care should be taken to avoid placing it close to room lights.

It should be appreciated by the person skilled in the art that although the discussion relates to a portable kinetic fluorometer, it is easily envisioned that the microfluidic cassettes and method described herein can be used on a kinetic fluorometer in a laboratory. Further, it is easily envisioned that sunlight can be used as the light source and if the detector is a solar cell detector, a totally passive device that does not use battery power can be created that is still capable of an opto-electronic measurement.

Microfluidic Cassettes

Essentially, the cassette includes: a) separate chambers for cell-laden and cell-free sample; and b) the chambers must be monitored in a such way that there is no cross-talk, i.e., light exiting one of the chambers must not reach the photodetector for the second chamber. If this happens, it distorts the results (non-linear slopes) and decreases sensitivity. This could be avoided by introducing light barriers between the chambers.

The microfluidic cassette is a fully enclosed acrylic cuvette. The cuvette comprises an acrylic sheet where the channels and chambers are cut. In the example, acrylic was used, but it should be appreciated that any visible range transparent polymer with no or minimal haze can be used provided that it is joined using thermal or pressure (physical) bonding. Adhesive bonding interferes with the indicator so is preferably not used. In addition to acrylic, other materials that can be used include, but are not limited to, polystyrene, polycarbonate, polyesters, celluloids (e.g., cellulose acetate or similar cellulosic derivatives), and any other thermoplastic or thermoset optical resins. The acrylic sheet can have a depth of about 1 mm to about 3 mm, preferably above 1 mm to about 2 mm, and most preferably about 1.5 mm. The acrylic sheet is then covered on the top and on the bottom with a thin layer of poly(methyl methacrylate) (PMMA) or polystyrene to form a fully enclosed cuvette. The thin layers can be each about 0.2 mm thick. It should be appreciated by the person skilled in the art that the cuvette can be one layer if 3D printing is used, two layers if the channels are engraved and not cut through from the top to the bottom of the acrylic sheet, or even more layers if other functions are added. The chemical composition of the microfluidic cassette is important. Specifically, the "glue" that is used to attach the acrylic sheet to the PMMA or polystyrene layers must not react with the indicator and must not deteriorate the optical quality of the surfaces. Accordingly, adhesives are preferably not used and the cassette is sealed by pressure, temperature, and weak solvent assistance. If PMMA is used in the cuvette, chloroform, acetone or similar are to be avoided. The weak solvent used can be ethanol, which not only helps to bond the device, but also sterilizes it. Other weak solvents include, but are not limited to, methanol/water, dimethyl sulfoxide/water, ethyl acetate/water. In general, any organic solvents that do not dissolve the plastic well and evaporate completely during the bonding are possible to be used. It should be appreciated that the solvents used is specific for a given polymer (i.e., PMMA or polystyrene). The microfluidic cassette can be heat treated to bond the layers, as readily understood by the person skilled in the art.

The microfluidic cassette of the inventions has two channels, each channel leading to at least one chamber, wherein one chamber is for the sample-derived negative control and one chamber is for the sample. The present inventors found that it's important to have a negative control since some samples (e.g., samples comprising Vitamin C, caffeine and other samples that react with NADH) might have the same reduction effect on the indicator dye, resulting in a false positive. The difference between the change in fluorescence between the sample and the sample-derived negative control correlates to the number of colony forming units per milliliter in the sample. It should be appreciated that although the description of the sample-derived negative control is specific to fluorescence that the importance of the sample-derived negative control can be extended to other detection means (e.g., absorbance, temperature, pressure, pH, conductivity and/or image processing) to eliminate problems with false positives.

Figure 5:
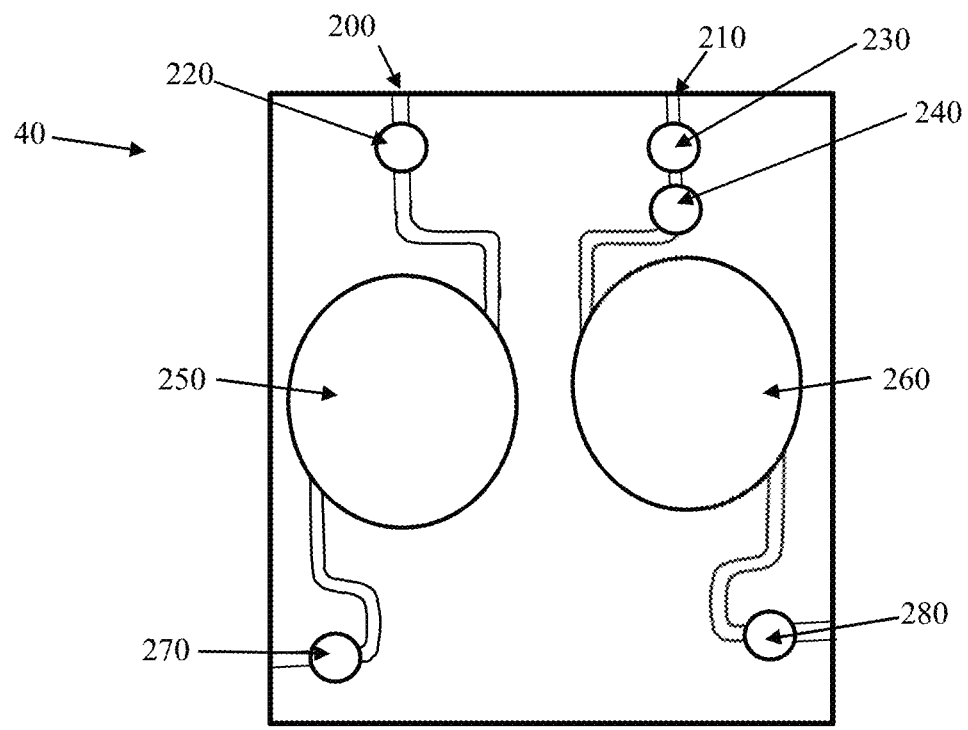
FIG. 5 is a schematic of still another embodiment of the microfluidic device of the invention.

A first embodiment of the dual channel microfluidic cassette 40 is illustrated in FIG. 5. Each channel 200, 210 communicatively connects to a chamber 250, 260, respectively. Notably, FIG. 5 includes a filter 240 in the right channel, but the filter is optional in the cassette of FIG. 5, as the sample-derived negative control can be prepared (e.g., filtered or centrifuged) prior to introduction to channel 210. The filter is chosen to capture cells by having pores of about 0.2 microns or less. The cassette 40 further includes injection ports 220, 230, 270, and 280, wherein the injection ports can be septa ports which can be pierced. Alternatively, the ports can be drilled in the sides of the cassette and filled with silicone, thereby acting like a septum. The microfluidic cassette 40 of FIG. 5 is preferably designed so as to provide air free filling via capillary force. Notably, the embodiment illustrated is FIG. 5 is not intended to limit the device design in any way and the channels and chambers may be perfected to satisfy the design preferences. Moreover, it is easily envisioned by the person skilled in the art that a light barrier can be inserted in the cassette between the chambers to minimize any cross talk between the chambers.

In practice, the cassette 40 of FIG. 5 can be filled by attaching needles to ports 220 and 270 and injecting the sample into chamber 250, wherein port 270 acts as a vent to minimize air in the cassette. Needles can be attached to ports 230 and 280 and either (a) a pre-filtered sample-derived negative control can be injected into the chamber 260, or (b) a filter 240 is present in the channel 210 and sample is injected into port 230, wherein the filter captures cells such that the sample-derived negative control is generated in chamber 260. Port 280 acts as a vent to minimize air in the cassette. Additionally, to minimize bubbles in the chamber, which can lower sensitivity, the channels preferably have a small cross-section.

Figure 3:
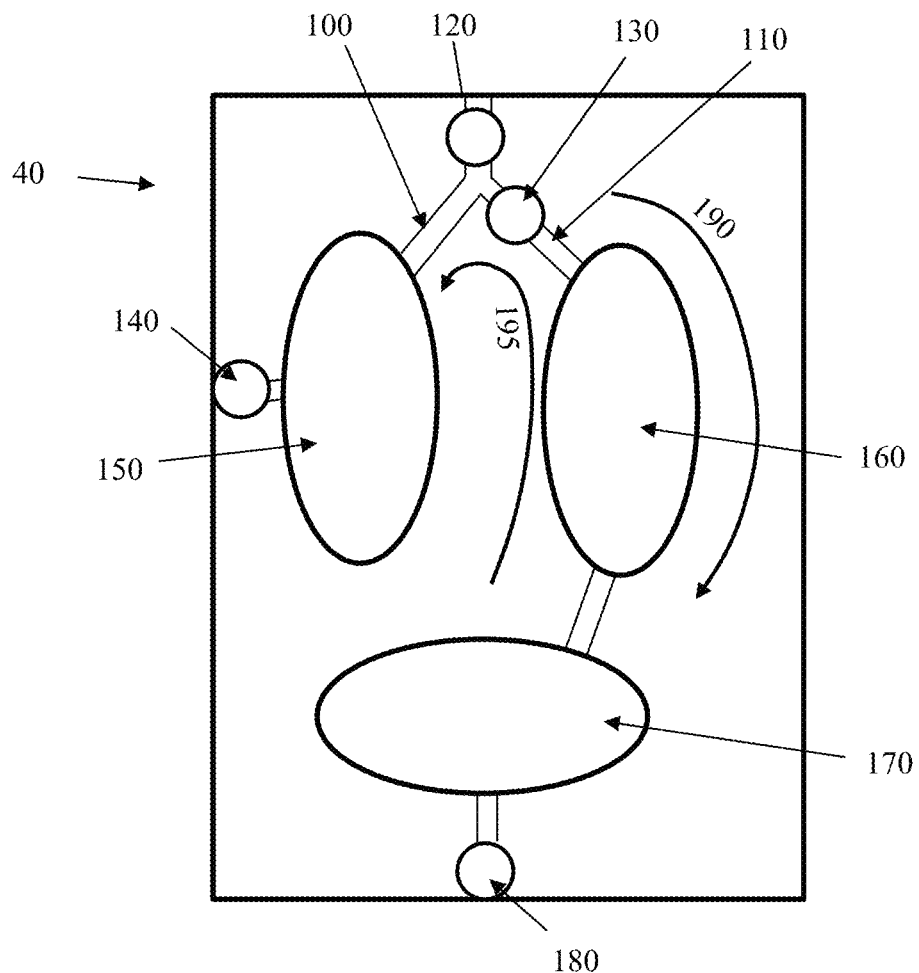
FIG. 3 is a schematic of one embodiment of the microfluidic device of the invention.

Another embodiment of the cassette 40 is shown in FIG. 3. As indicated, there are two channels 100, 110 in the cassette of the invention, wherein channel 100 communicatively connects to chamber 150 and channel 110 communicatively connects to chamber 160, which is communicatively connected to chamber 170. In other words, in the embodiment of FIG. 3, one of the two channels feeds at least two chambers. Further, the microfluidic cassette 40 comprises a filter 130 and injection ports 120, 140, 180. The filter is chosen to capture cells by having pores of about 0.2 microns or less, and the injection ports can be septa ports which can be pierced. Alternatively, the ports can be drilled in the sides of the cassette and filled with silicone, thereby acting like a septum. It is easily envisioned by the person skilled in the art that a light barrier can be inserted in the cassette between the chambers to minimize any cross talk between the chambers.

Figure 4:
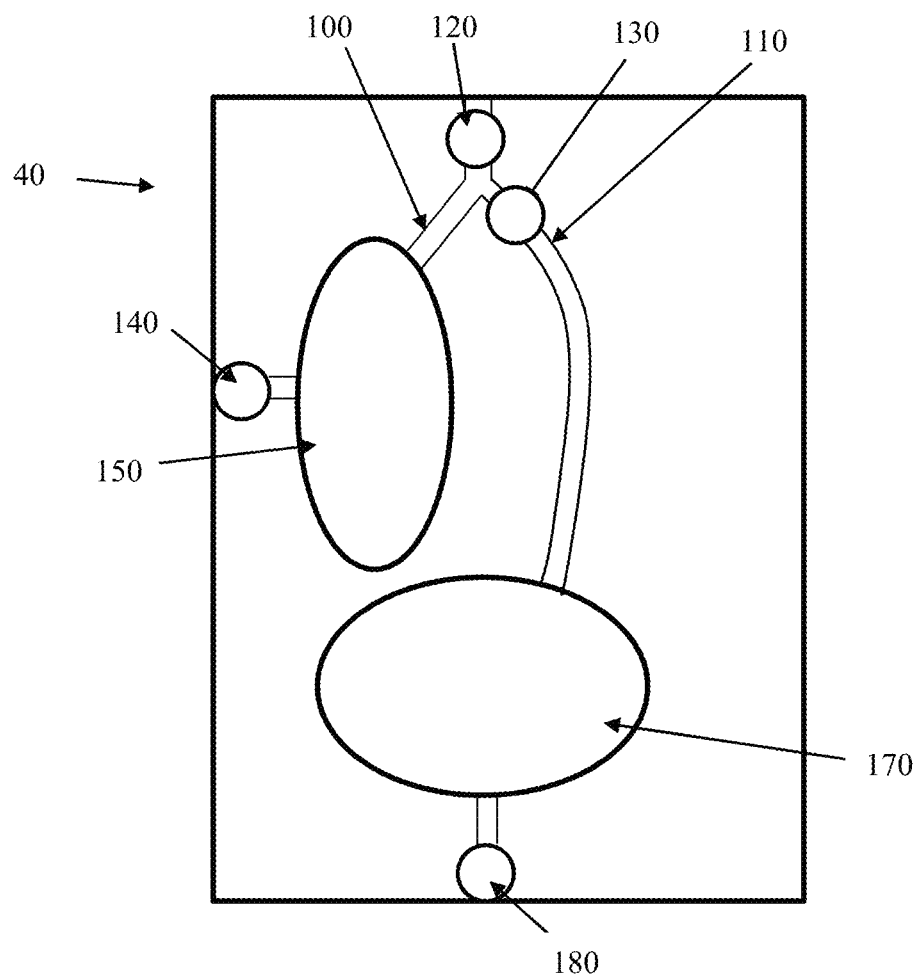
FIG. 4 is a schematic of another embodiment of the microfluidic device of the invention.

Still another embodiment of the cassette 40 is shown in FIG. 4. The cassette of FIG. 4 is almost identical to the cassette of FIG. 3 instead there is just one chamber associated with channel 110. It is easily envisioned by the person skilled in the art that a light barrier can be inserted in the cassette between the chambers to minimize any cross talk between the chambers.

In phase one 190 of the loading of the sample in the microfluidic cassette of FIGS. 3 and 4, needles are attached to ports 120 and 180 and the sample entering at port 120 fills chamber 150 and also passes through filter 130 and fills chambers 160 and 170 (or just chamber 170 in FIG. 4). Any cells that may be in the sample accumulate on the side of the filter 130 closest to port 120 and as such, the liquid contained in chambers 160 and 170 are cell-free (i.e., bacteria free) and serve as the sample-derived negative control. In phase two 195, needles or other piercing means are attached at ports 180 and 140 and air is injected via port 180 to "blow" the bacteria back into chamber 150. This method has the advantage of doubling or tripling the concentration of cells in the sample in chamber 150 (if any viable cells are present in the sample), thereby increasing the sensitivity of the process.

In general, the experiments performed by the inventors suggest that the three-chamber cassette of FIG. 3 is more sensitive than the two-chamber cassette of FIG. 4 when only one sample is being tested. If the intent is to test more than one sample, the cassette can be adapted to include more chambers, as readily understood by the person skilled in the art.

Preparation of the Cells

To test the device of FIG. 5, *E. coli* cells were used. Initially, 100 mL primary culture was prepared using 10 μL of *E. coli* NM303 cells, which were grown at 37° C. in a shaker at 150 rpm for 8 hours until the optical density of primary culture was measured to be 2.5 at 600 nm The primary seed culture (1%) was used to inoculate 200 mL of secondary culture grown at 37° C. in a shaker at 150 rpm to reach an optical density of 0.4 at 600 nm. This sample was used for making serial dilutions to get the concentration of 1000 CFU/mL. Then, 1 mL of the resulting solution is mixed with 5 μL of resazurin dye to be tested by the system. The dye was prepared as previously described by Al-Adhami, M., et al. [18].

Measurement of Resazurin Reduction 1 mL of the cell culture with the respective number of CFU is deposited in an EPPENDORF tube. Then, 3.3 μl of freshly made reaction mix is added to it and the final mixture is vortexed and 300 μl, are injected into the microfluidic cassette of FIG. 5. The reaction mix comprises PBS and resazurin stock solution. Two needles are used on the both sides of the cassette. The first needle is used to inject the mix, while the second needle serves as a vent for the air. A sample-derived negative control is also prepared wherein some amount of the final mixture is filtered and the filtrate is injected into the other chamber of the cassette, analogous to how the sample is injected. After withdrawing the needles, the cassette is inserted into the kinetic fluorometer cassette holder.

Once the cassette is in the device, a control program is started (as discussed in [18]). It continuously measures and displays the fluorescence intensity. The control program also calculates the running value of the slope of the fluorescence intensity change. If the slope is substantially zero, there is no contamination. If the slope is significant, the media is contaminated.

Figure 6:
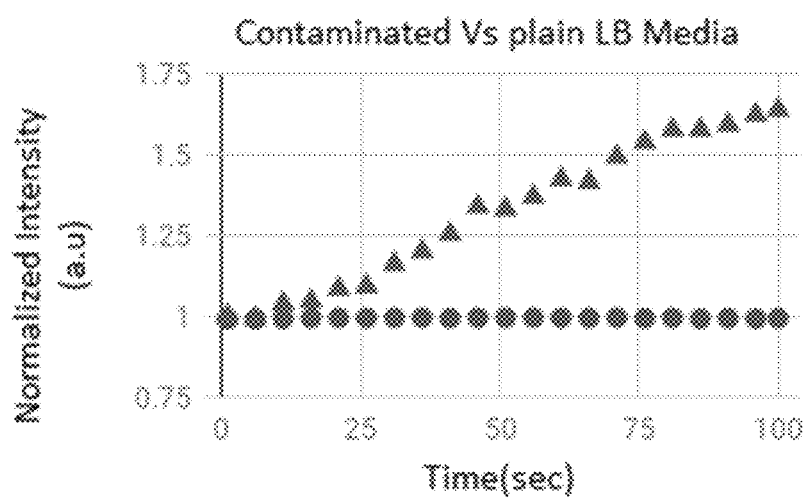
FIG. 6 shows the results of the sample relative to the sample-derived negative control from Example 1.

FIG. 6 shows the results of the sample relative to the sample-derived negative control. It can be seen that the sample-derived negative control has a slope of substantially zero while the sample has a positive slope. By comparing the difference of fluorescence intensity with time, we are able to correspond the slopes with the number of viable cells in the sample.

Example 2

Figure 7:
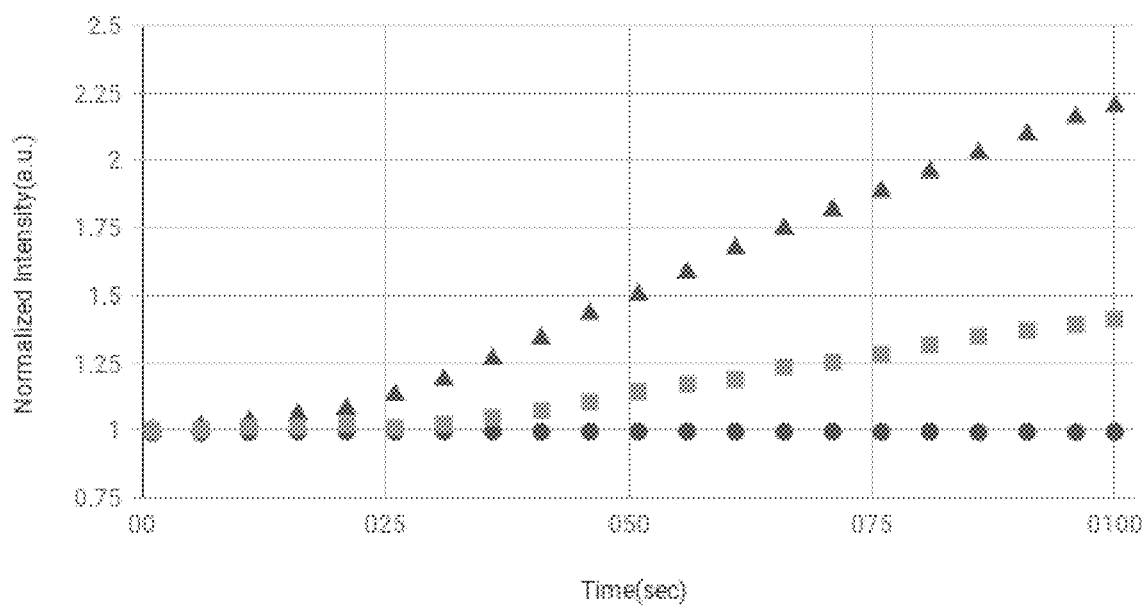
FIG. 7 illustrates the importance of having a sample derived negative control by comparing the fluorescence intensity of filtered versus non-filtered Kombucha tea.

Kombucha tea was studied to emphasize the importance of the differential study of contamination in samples. Kombucha has caffeine and live cultures in which both are reducing agents. 1 mL of the Kombucha cell culture with the respective number of CFU is deposited into an EPPENDORF tube. Then, 5 μL of the freshly made resazurin dye mix is added to it. The final mixture is mixed and 300 μL are injected into the microfluidic cassette of FIG. 5 and inserted into the kinetic fluorometer cassette holder. Once the cassette is in the device, the control program is started. FIG. 7 shows the importance of having the negative control embedded into the system. Unlike a regular cell culture, Kombucha yeast is cultured in tea. It is natural for the tea to have caffeine which is a known antioxidant. Antioxidants can cause a similar reaction with the resazurin dye as bacteria. The difference in slopes between the filtered and non-filtered samples determines the presence of contamination.

Example 3

The device is also used to automatically detect contamination in drinking water. The fluidic system consists of a 1 L water tank that is continuously being stirred and has an outlet at the bottom. The outlet is connected to a syringe pump equipped with a 60 mL syringe. The syringe pump will pull the water out of the tank to be stored in the syringe. A second syringe pump containing the LB media/Resazurin mix is prepared. The two pumps run simultaneously and mix via a microfluidic mixer. The mixed sample is then divided into two parts. 1 ml goes through a 0.2 μm filter to make sure it doesn't contain bacteria while the bacteria containing sample is deposited directly into the reading cuvette. When the sample is loaded into the microfluidic cassette, the device will take readings for 5 minutes to determine the difference between the two samples. The difference (if any) will determine the existence or lack of bacteria in the sample.

Example 4

A differential reading could also be obtained by examining the change in absorbance. This method could be done electronically wherein the metabolic activity of contaminants changes the indicator dye, and by studying the difference in absorbance between the sample and the sample-derived negative control, any contamination can be detected. Traditionally, absorbance is done using a UV-Vis Spectrophotometer. A quick way to measure absorbance is using a mobile phone. Once the chambers are filled with the sample and the sample-derived negative control, the flash of the phone can be used as the light source while the phone camera can be the light sensor. By recording the dye absorbance change over a set amount of time and examining the difference, contamination can be detected. Using absorbance to detect the metabolic rate of viable cells will show the existence of contamination or the lack thereof but not concentration. Accordingly, it is useful in the field for a rapid, point-of-use measurement only.

Example 5

By treating a contaminated sample with antibiotics, it is possible to determine antibiotic susceptibility. The sample can be split in half and one half of it is treated with antibiotics. Monitoring the differential rate allows the user to understand the effects of the antibiotic. Without the differential rate, it would only be possible to determine whether the antibiotic kills (e.g., no growth) or does not kill. With the differential rate, it is possible to observe dose-response effects (e.g., a little antibiotic slow the growth a lot of antibiotic kills all). In this case the untreated sample serves as a positive control, and the sample that is treated is the test sample. Eventually, for antibiotic testing we will develop a triple chamber device, with the first chamber used for positive control (no antibiotic, cells and indicator are present), the second will be used for negative control (antibiotic and indicator, but no cells—achieved by filtering the sample via 0.2 micron filter or centrifugation), and the third is the treated sample (cells, indicator and antibiotic). This configuration would be useful for antibiotics that may interact with the indicator. This feature hasn't been described in publication but it was disclosed.

As introduced above, if the intent is to test more than one sample, the cassette can be adapted to include more chambers, as readily understood by the person skilled in the art. Testing the efficacy of antibiotics is a good example of where a cassette with additional chambers will allow the experimenter to test 2, 3, 4, 5, 10, 15, 20, 25 or more antibiotics simultaneously. The only requirement is that there be a chamber for each antibiotic tested plus a chamber for the negative control.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

[1] Pharmtech.com (2015) An overview of rapid microbial-detection methods|Pharmaceutical technology. N.p. 2015. Web. 3 June 2015.
[2] Hoehl M M et al (2012) Rapid and robust detection methods for poison and microbial contamination. J Agric Food Chem 60 (25):6349-6358.
[3] Hobson N S, Tothill I, Turner A P (1996) Microbial detection. Biosens Bioelectron 11 (5):455-477.
[4] Fda.gov (2015) Archived BAM method: rapid methods for detecting foodborne pathogens. N.p. Web. 23 July 2015.
[5] Vogel S J, Tank M, Goodyear N (2013) Variation in detection limits between bacterial growth phases and precision of an ATP bioluminescence system. Lett Appl Microbiol 58 (4):370-375 Web.
[6] Celsis.com (2010) Quality control—microbial testing: rapid microbiological methods in lean manufacturing. N.p. Web. 23 July 2015.
[7] Pettit A C, Kropski J A, Castilho J L, Schmitz J E, Rauch C A, Mobley B C, Wang X J, Spires S S, Pugh M E (2012) The index case for the fungal meningitis outbreak in the United States. N Engl J Med 367(22):2119-2125.
[8] Gurramkonda C et al (2014) Fluorescence-based method and a device for rapid detection of microbial contamination. PDA J Pharm Sci Technol 68(2):164-171 Web.
[9] Estes C, Duncan A, Wade B, Lloyd C, Ellis W Jr, Powers L (2003) Reagentless detection of microorganisms by intrinsic fluorescence. Bio-sens Bioelectron 18(5):511-519.
[10] Bionity.com (2015) Alamarblue® assay for assessment of cell proliferation using the Fluos-tar OPTIMA. N.p. Web. 23 July 2015.
[11] Boyce S T, Anderson B A, Rodriguez-Rilo H L (2006) Quantitative assay for quality assurance of human cells for clinical transplantation. Cell Transplant 15(2):169-174.
[12] Boyce S T, Anderson B A, Rodriguez-Rilo H L (2006) Quantitative assay for quality assurance of human cells for clinical transplantation. Cell Transplant 15(2):169-174.
[13] Nagaoka M, Hagiwara Y, Takemura K, Mura-kami Y, Li J, Duncan S A, Akaike T (2008) Design of the artificial acellular feeder layer for the efficient propagation of mouse embryonic stem cells. J Biol Chem 283 (39): 26468-26476.
[14] Longhi M P, Wright K, Lauder S N, Nowell M A, Jones G W, Godkin A J, Jones S A, Galli-more A M (2008) Interleukin-6 is crucial for recall of influenza-specific memory CD4 T cells. PLoS Pathog 4(2):e1000006.
[15] Tanaka T Q, Williamson K C (2011) A malaria gameto-cytocidal assay using oxidoreduction indicator, alamar-Blue. Mol Biochem Parasitol 177(2):160-163.
[16] Hudman D A, Sargentini N J (2013) Resazurin-based assay for screening bacteria for radiation sensitivity. Springerplus 2(1):55.
[17] Fields R D, Lancaster M V (1993) Dual-attribute continuous monitoring of cell proliferation/cytotoxicity. Am Biotechnol Lab 11 (4):48-50.
[18] Al-Adhami, M et al., Rapid Detection of Microbial Contamination Using a Microfluidic Device, Biosensors and Biodetection: Methods and Protocols Volume 1: Optical-Based Detectors, Methods in Molecular Biology, vol. 1571, DOI 10.1007/978-1-4939-6848-0_18, 2017, Chapter 18.

What is claimed is:

1. A method of detecting the presence of viable cells in a sample, said method comprising:
    loading the sample in a microfluidic cassette, wherein the microfluidic cassette is used to separate the sample into two portions, a sample portion and a sample-derived negative control portion; and
    detecting a physical property of the sample portion and the sample-derived negative control portion and comparing same to determine a differential rate, wherein the differential rate is indicative of the presence of viable cells in the sample,
    wherein the microfluidic cassette comprises an inlet channel that splits into a sample channel and a sample-derived negative control channel, wherein the sample channel is communicatively connected to a sample chamber and the sample-derived negative control channel is communicatively connected to at least one sample-derived negative control chamber, wherein the inlet channel comprises an inlet port upstream of the split, a first port downstream of the sample chamber, and a second port downstream of the sample-derived negative control chamber(s), and wherein the microfluidic cassette comprises a filter along the sample-derived negative control channel positioned between the split and the sample-derived negative control chamber(s).

2. The method of claim 1, wherein the sample-derived negative control portion corresponds to the sample where any viable cells have been inactivated or removed.

3. The method of claim 1, wherein the sample comprises water and may contain other substances that are soluble or dispersed in water.

4. The method of claim 1, wherein the physical property detected is fluorescence, absorbance, temperature, pressure, pH, conductivity and/or image processing.

5. The method of claim 1, wherein the filter permits an increase in viable cells in the sample chamber, thereby increasing sensitivity of the detecting.

6. The method of claim 1, wherein the physical property detected is fluorescence and an indicator dye is injected into the sample portion and the sample-derived negative control portion.

7. The method of claim 6, wherein the indicator dye comprises resazurin.

8. The method of claim 1, wherein the detecting takes place over time in a range from about 1 minute to about 240 minutes.

9. The method of claim 1, wherein the physical property detected is fluorescence and two single-excitation, single-emission photometers are used, one for the sample portion and the other for the sample-derived negative control portion.

10. The method of claim 1, wherein the sample-derived negative control channel further comprises a second sample-derived negative control chamber positioned between a first sample-derived negative control chamber and the second.

11. The method of claim 1, wherein the loading comprises:
attaching a needle to the inlet port and a needle to the second port,
injecting the sample in the inlet port such that the sample fills the sample chamber and also passes through the filter and fills the sample-derived negative control chamber(s);
attaching a needle to the first port and a needle to the second port;
injecting air in the second port to remove cells from the filter and introduce them to the sample chamber for detection therein.

12. The method of claim 1, wherein the microfluidic cassette further comprises a light barrier positioned between the sample chamber and the sample-derived negative control chamber(s).

13. The method of claim 1, wherein each port has a septum.

14. The method of claim 1, wherein the physical property detected is fluorescence and an excitation light path and an emission light path are oriented at 90° at each other.

* * * * *

UNITED STATES PATENT AND TRADEMARK OFFICE
CERTIFICATE OF CORRECTION

PATENT NO. : 10,948,414 B2
APPLICATION NO. : 16/000935
DATED : March 16, 2021
INVENTOR(S) : Govind Rao et al.

Page 1 of 1

It is certified that error appears in the above-identified patent and that said Letters Patent is hereby corrected as shown below:

In the Claims

Column 15, Line 24, In Claim 10: sample-derived negative control chamber and the second.
CORRECTION: sample-derived negative control chamber and the second port.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*